(12) United States Patent
Most et al.

(10) Patent No.: US 9,980,518 B1
(45) Date of Patent: May 29, 2018

(54) HEATING ELEMENT FOR A PORTABLE VAPORIZER

(71) Applicants: Matthew Isaac Most, Boulder, CO (US); Trevor Glen Vita, Boulder, CO (US)

(72) Inventors: Matthew Isaac Most, Boulder, CO (US); Trevor Glen Vita, Boulder, CO (US)

(*) Notice: Subject to any disclaimer, the term of this patent is extended or adjusted under 35 U.S.C. 154(b) by 444 days.

(21) Appl. No.: 14/959,851

(22) Filed: Dec. 4, 2015

Related U.S. Application Data

(60) Provisional application No. 62/087,749, filed on Dec. 4, 2014, provisional application No. 62/087,751, filed on Dec. 4, 2014, provisional application No. 62/088,048, filed on Dec. 5, 2014, provisional application No. 62/087,747, filed on Dec. 4, 2014.

(51) Int. Cl.
| | | |
|---|---|---|
| *A24F 47/00* | (2006.01) | |
| *H05B 3/44* | (2006.01) | |
| *A61M 15/00* | (2006.01) | |
| *H05B 1/02* | (2006.01) | |
| *H05B 3/04* | (2006.01) | |
| *H05B 3/14* | (2006.01) | |
| *A61M 11/00* | (2006.01) | |
| *H05B 3/20* | (2006.01) | |
| *H05B 3/08* | (2006.01) | |

(52) U.S. Cl.
CPC ....... *A24F 47/008* (2013.01); *A61M 15/0001* (2014.02); *H05B 3/08* (2013.01); *H05B 3/141* (2013.01); *H05B 3/20* (2013.01); *A61M 2205/36* (2013.01)

(58) Field of Classification Search
CPC ........... A24F 47/008; H05B 6/36; H05B 3/16; H05B 6/108; H05B 3/04; H05B 3/141; H05B 3/146; H05B 3/44; H05B 1/0252; H05B 2203/021; H05B 2203/022; H05B 2203/037; H05B 2203/013
USPC ......................................... 392/387, 395, 403
See application file for complete search history.

(56) References Cited

U.S. PATENT DOCUMENTS

| | | | | |
|---|---|---|---|---|
| 4,429,703 | A * | 2/1984 | Haber | A24F 47/002 131/273 |
| 8,550,068 | B2 * | 10/2013 | Terry | A24F 47/008 128/200.12 |
| 9,022,026 | B2 * | 5/2015 | Fang | A24F 47/008 128/202.21 |
| 9,204,670 | B2 * | 12/2015 | Liu | A24F 47/008 |
| 9,259,035 | B2 * | 2/2016 | Terry | A24F 47/008 |
| 9,271,527 | B2 * | 3/2016 | Liu | A24F 47/002 |
| 9,775,379 | B2 * | 10/2017 | Davidson | A61M 15/0003 |
| 2008/0092912 | A1 * | 4/2008 | Robinson | A24F 47/008 131/200 |
| 2011/0126848 | A1 * | 6/2011 | Zuber | A24F 47/008 131/329 |

(Continued)

*Primary Examiner* — Eric Stapleton
(74) *Attorney, Agent, or Firm* — Marsh Fischmann & Breyfogle LLP; Russell T. Manning

(57) ABSTRACT

Presented herein is a compact air heat exchanger/heating element for use in a portable vaporizer. In one arrangement the heating element is a multi-layered ceramic element having multiple internal conductive layers that form resistors. The heating element may be manufactured utilizing Low-Temperature Co-Fired Ceramic (LTCC) and Printed Circuit Board (PCB) manufacturing processes.

19 Claims, 9 Drawing Sheets

(56) References Cited

U.S. PATENT DOCUMENTS

| | | | | |
|---|---|---|---|---|
| 2012/0304990 A1* | 12/2012 | Todd | A61M 11/042 | 128/203.14 |
| 2013/0152922 A1* | 6/2013 | Benassayag | A61M 15/06 | 128/202.21 |
| 2013/0276799 A1* | 10/2013 | Davidson | A24F 47/004 | 131/273 |
| 2014/0000638 A1* | 1/2014 | Sebastian | A24F 47/008 | 131/328 |
| 2014/0041655 A1* | 2/2014 | Barron | A61M 11/042 | 128/202.21 |
| 2014/0060556 A1* | 3/2014 | Liu | A24F 47/008 | 131/329 |
| 2015/0173124 A1* | 6/2015 | Qiu | A24F 47/008 | 131/328 |
| 2016/0089508 A1* | 3/2016 | Smith | A61M 15/06 | 128/200.16 |

* cited by examiner

HEATING ELEMENT FOR A PORTABLE VAPORIZER

CROSS-REFERENCE

The current application claims the benefit of the filing date of U.S. Provisional Application No. 62/087,749 having a filing date of Dec. 12, 2014, the entire contents of which is incorporated herein by reference.

FIELD

The present disclosure relates generally to vaporizers. More specifically, the present disclosure relates to an improved heat exchanger/heating element for use in heating herbs to extract active ingredients of the plant material by vaporization.

BACKGROUND

In a number of applications, individuals extract the active ingredients of plant materials such as tobacco, herbs, oil and other beneficial materials (hereafter 'herbs' or 'herb material') to treat a variety of conditions. Typically, the extracted ingredients are then delivered via inhalation to the individual. A vaporizer is a device used to extract the active ingredients of herbs for inhalation. Vaporization involves heating an herb material so that its active compounds boil off into a vapor. As opposed to smoking, i.e., burning, vaporization avoids the production of irritating, toxic, and carcinogenic by-products as no combustion occurs.

There are two main heating types for vaporization: conduction and convection. In conduction heating, heat is transferred directly to the herb material. That is, a heating element transfers heat directly to herb material physically contacting the heating element. In convention heating, air is heated to a desired temperature and then passed through herb material to be vaporized.

Convection type vaporizers employ an airflow heating element/heat exchanger that heats air passing through the heating element to a vaporization temperature, which allows extracting active ingredients from the herb material. To extract active ingredients of most herbs utilizing convection heating, the vaporization temperature of the heated air is generally between about 275 and about 400 degrees Fahrenheit. However, the vaporization temperature varies depending on the type of herb material.

Users of vaporizers often prefer the devices to be portable. In this regard, users tend to prefer vaporizers having a small form factor similar in size to a pen or electronic cigarette. However, due to the high temperatures required to vaporize herbs, significant amounts of electrical power are required. Along these lines, prior art battery powered vaporizers are effective for only a small number of uses per charge. To provide a small, portable vaporizer that allows for numerous uses, it is desirable that the heating element/heat exchanger be small, efficient and capable of generating necessary vaporization temperatures.

SUMMARY

Provided herein are compact heating elements/heating exchangers having high power handling capabilities. In some arrangements, the heating elements leverage Low-Temperature Co-fired Ceramic (LTCC) and Printed Circuit Board (PCB) fabrication processes to allow production of ultra-compact heating elements. In one specific arrangement, the heating element is a circular PCB manufactured using LTCC process equipment. Various arrangements of the presented heating elements are novel by themselves.

In one aspect, the novel heating element is combined with a portable vaporizer. The body of the vaporizer houses a power source. An herb vaporization chamber is attached to an end of the vaporizer housing. An inlet to the herb vaporization chamber is in fluid communication with an air inlet port of the vaporizer. An outlet of the herb vaporization chamber is in fluid communication with an outlet port of vaporizer. Disposed within the airflow path between the inlet of the herb chamber and the outlet of the herb chamber is a convective heating element. The convective heating element is selectively connectable to the power source to heat air passing through the herb chamber for purposes of vaporization.

The convective heating element includes an air inlet end and an air outlet end. In one non-limiting arrangement, the heating element is a cylindrical heating element and the air inlet and outlet ends of the heating element are circular. However, it will be appreciated that other shapes may be utilized. In any arrangement, the convective heating element includes a plurality of spaced conductive layers/conductors disposed between its air inlet and outlet ends. These conductors are substantially parallel to one another and most commonly parallel to the air and inlet/outlet ends. Furthermore, the conductors are electrically connected in at least a first resistive network to provide heat in response to application of a voltage/current from the power source. In addition, a plurality of through holes extend through the convective heating element between its inlet end and outlet end. Most commonly, the plurality of through holes are substantially perpendicular to both the conductors and the inlet and outlet ends of the heating element.

The conductor layers are separated by insulating layers. That is, at least one insulating layer is disposed between each adjacent pair of conductor layers. In one arrangement, the insulating layers and conductor layers are formed of co-fired ceramic tape layers and thick film conductors printed on the ceramic tape layers prior to firing the ceramic tape layers. In such an arrangement, conductors may be printed onto a green tape in a desired pattern and one or more apertures may be formed through each green tape. Accordingly, a plurality of green tape layers may be formed, stacked, compressed and fired to form a monolithic heating element having a plurality of internal conductive layers. In various arrangements, conductive vias may extend between the conductor layers to form a resistive network of conductor layers.

In various arrangements, the heating element may have a plurality of conductor layers and each of these layers may be combined with one or more additional conductors to form one or more circuits. Furthermore, separate circuits may be formed within the heating element. These circuits may be connected in series and or parallel to provide desired characteristics for the heating element.

When producing a highly compact heating element for use with a vaporizer, the heating element may have a maximum cross-dimension (e.g., diameter) of less than 15 mm and more preferably of less than 10 mm. In any arrangement, it is desirable that the total mass of the heating element be reduced. In this regard, it may be preferable to provide numerous through holes to allow for improved air flow as well as reducing the thermal mass of the heating element. In one arrangement, the through holes have a combined volume of over one third the total volume within the spatial envelope defined by the heating element. In another arrangement, is preferable that the combined internal surface area (e.g., heated area) of the through holes may be 5 to 20 times the area of the air inlet surface of the heating element.

DETAILED DESCRIPTION

Reference will now be made to the accompanying drawings, which at least assist in illustrating the various pertinent features of the presented inventions. The following description is presented for purposes of illustration and description and is not intended to limit the inventions to the forms disclosed herein. Consequently, variations and modifications commensurate with the following teachings, and skill and knowledge of the relevant art, are within the scope of the presented inventions. The embodiments described herein are further intended to explain the best modes known of practicing the inventions and to enable others skilled in the art to utilize the inventions in such, or other embodiments and with various modifications required by the particular application(s) or use(s) of the presented inventions.

Figure 1A:
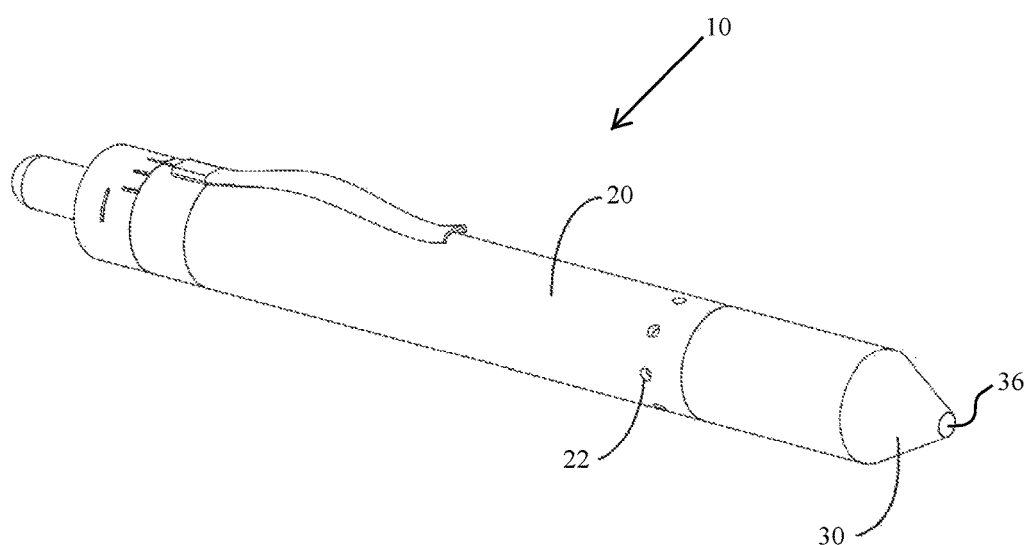
FIG. 1A is a perspective view of one embodiment of a vaporizer.

FIG. 1A illustrates a perspective of a portable vaporizer 10 for extracting active ingredients of herbs for inhalation. The vaporizer 10 is similar in size and form to a fountain pen. As shown, the vaporizer 10 includes a cylindrical body 20 and a mouthpiece 30. The mouthpiece 30 tapers to an opening 36 that a user utilizes to draw air into the vaporizer via air inlet apertures 22 in the cylindrical body 10. More specifically, the air is drawn through the interior of the vaporizer 10 where it passes through an internal heating element/heating exchanger, which heats the air to a desired temperature. The heated air passes through an internal herb chamber which holds a supply of herbs, which may be at least partially vaporized. The user draws the resulting vapor through the opening 36 in the mouth piece.

Figure 1B:
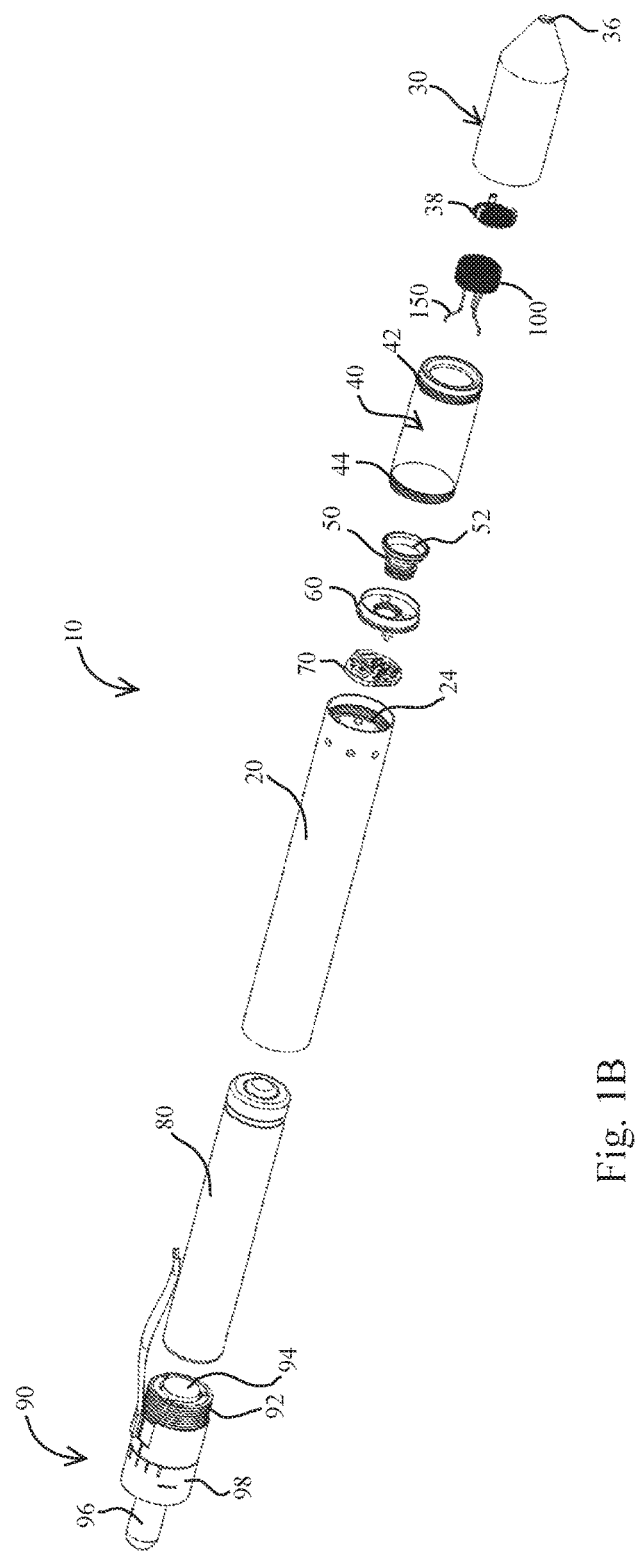
FIG. 1B is an exploded perspective view of the vaporizer of FIG. 1A.
Figure 1C:
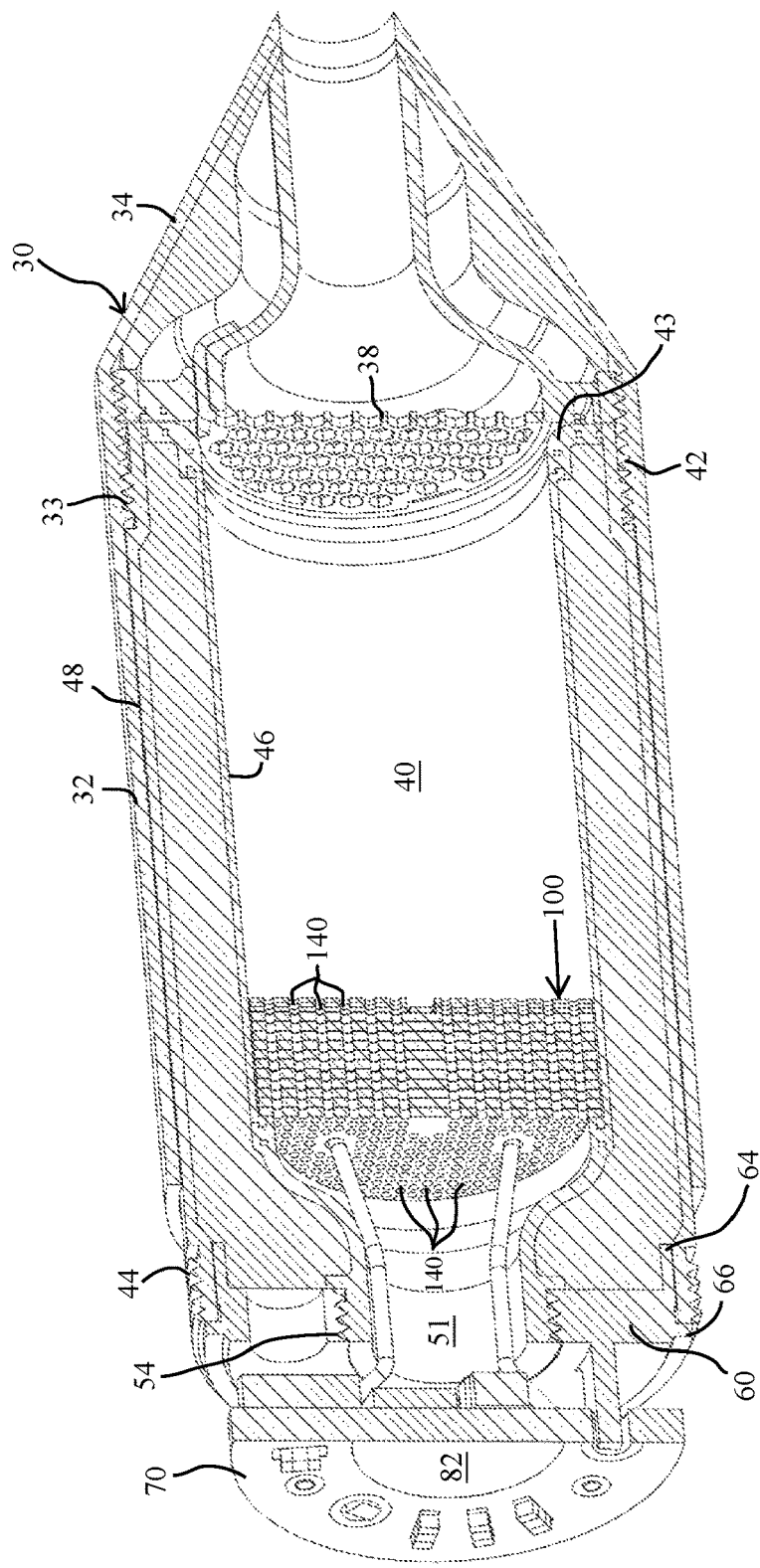
FIG. 1C is cross-sectional perspective view of a forward portion of the vaporizer of FIG. 1A.

FIG. 1B illustrates an exploded perspective view of the vaporizer 10 and FIG. 1C illustrates a cross-sectional view of an assembled forward portion of the vaporizer 10. As shown, the mouthpiece 30 is formed of a generally hollow cylindrical section 32 attached to a conical end section 34. The mouthpiece 30 includes internal threads 33 located near the transition between the cylindrical section 32 and the conical end section 34 as best shown in FIG. 1C. These internal threads 33 engage external threads 42 located on the forward end of a generally hollow herb chamber 40. External threads 44 on a rearward end of the herb chamber attach to internal threads 24 on a forward end of the cylindrical body 20. See FIG. 1B. In the present embodiment, when the mouthpiece 30 is in threaded engagement with the herb chamber 40, the cylindrical section 32 of the mouthpiece 30 extends over the herb chamber 40 and abuts with the forward end of the cylindrical body 10. See FIG. 1A.

Referring again to FIGS. 1B and 1C, a rearward interior portion of the herb chamber 40 houses a heating element 100, when the vaporizer 10 is assembled. A forward portion of the herb chamber 40 (i.e., in front of the heating element) provides an open internal space for placement of herbs. The heating element 100 is a convective heating element which heats air drawn into the herb chamber 40 from the air inlet apertures 22 in the cylindrical body. As illustrated, a screen 38 may be disposed within the mouthpiece 30 to prevent any particulate from passing through the device. In a further embodiment another screen (not shown) may be disposed within the herb chamber 40 proximate to the heating element 100.

An air nozzle 50 is positioned against a rearward end of the heating element 100 as best shown in FIG. 1C. The nozzle 50 extends from a small inlet aperture 51 (See FIG. 1C) to a larger exit aperture 52 (see FIG. 1B), juxtaposed against the rearward end of the heating element 100 to fluidly connect the inlet apertures 22 to the heating element 100, when the herb chamber 40 is in threaded connection with the cylindrical body 20. In the present embedment, external threads 54 on a rearward end of the air nozzle 52 connect with internal threads of a mount 60 having a flange 64 received within the rearward end of the herb chamber 40. When assembled, the herb chamber 40 compresses a rim 66 of the mount 60 between against the bottom of the internal threads 24 of the forward end of the cylindrical body 10. A rearward surface of the mount 60 supports a forward electronics control circuit or forward circuit board 70. Connecting wires 150 (e.g., power wires, sensor wires etc.) of the heating element 100 pass through the air nozzle 50 for connection with the forward circuit board 70. Other connections are possible.

Figure 1D:
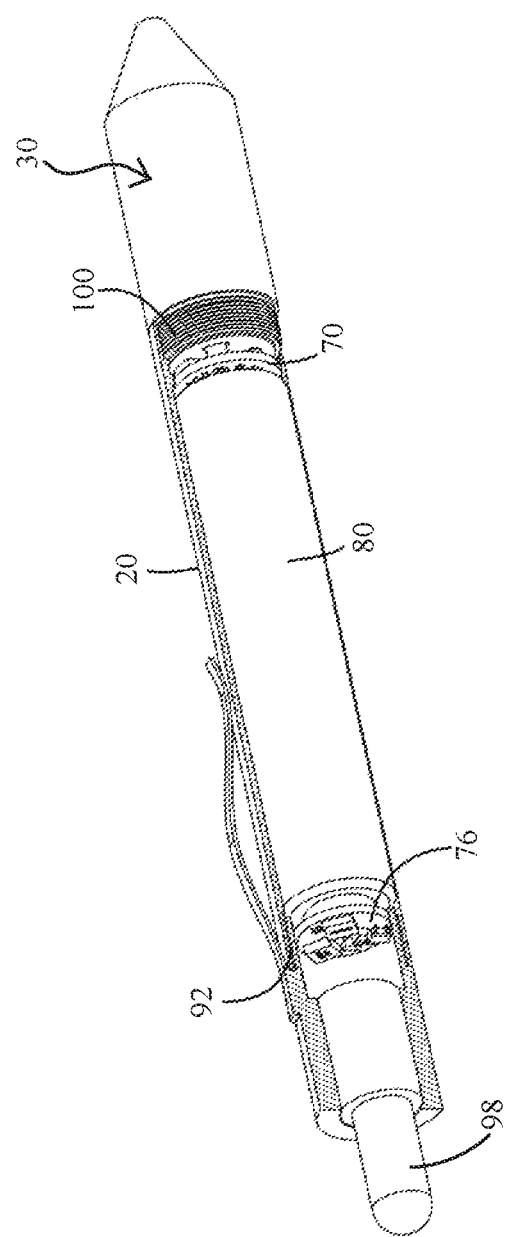
FIG. 1D is cross-sectional perspective view of a rearward portion of the vaporizer of FIG. 1A.

The cylindrical body 20 houses a battery 80 in its rearward portion behind the air inlet apertures 22. See FIG. 1B. An end cap assembly 90 having external threads 92 engages internal threads (not shown) on a rearward portion of the cylindrical body 20. When the end cap assembly 90 is in threaded engagement with the cylindrical body 20, a forward terminal of the battery 80 engages a first electrical contact 82 of the forward circuit board 70 and a second contact 94 of the end cap assembly 90 engages a rearward terminal of the battery 80. The end cap assembly 90 includes a power button 96 that allows for activating and deactivating the device 10 (i.e., completing an electrical circuit). Additionally, the end cap assembly 90 further includes a temperature adjustment dial 98, which allows for adjusting the temperature of air passing through the device. In one embodiment, the end cap assembly 90 further includes a rearward circuit board 76 which cooperates with the forward circuit board 70 to control the operation of the vaporizer 10. See FIG. 1D. Further details the operation of the control circuits of the vaporizer 10 are described in a co-filed U.S. Patent Application claiming priority to U.S. Provisional Patent Application No. 62/087,747.

As shown in FIG. 1C, the herb chamber is a double walled chamber having an internal housing 46 and an external housing 48. The internal housing 46 has a smaller diameter than the external housing 48 to define a chamber there between. The chamber at least partially thermally isolates the exterior of the herb chamber from the heated air within the chamber. Along these lines, it is noted that the temperatures required for vaporization (e.g., 275 to 400 degrees Fahrenheit) within the chamber could result in significant temperatures being applied to the internal housing 46. To further reduce the transfer of thermal energy to the exterior housing 48, the chamber may be filled with insulation.

In use, a user removes the mouthpiece 30 from the herb chamber 40. Herbs are then placed within the forward portion of the herb chamber 40 in front of the heating element 100. At this time, a user may select a temperature setting using the temperature adjustment dial 98 and to press the power button 96. The control circuitry then supplies electrical power to the heating element 100. Once the heating element achieves a desired temperature an indicator light (not shown) is illuminated to indicate that the vaporizer is ready for use. At this time, the user may draw air through the opening 36 in the mouthpiece, which draws air through the inlet apertures 22, through the nozzle 50, through the heating element 100 and through herbs within the herb chamber 40. The user receives vapors through the opening 36.

The high temperatures needed to vaporize active ingredients of the herbs within the herb chamber 40 require significant electrical power be provided to a small form factor heating element/heat exchanger (hereafter 'heating element'). Further, the inventors have recognized that such a heating element should attempt to reduce or minimize pressure losses and reduce or minimize thermal mass to improve efficiency. To provide such a heating element, the presented heating element design leverages Low-Temperature Co-fired Ceramic (LTCC) and Printed Circuit Board (PCB) fabrication processes. The result is an extremely compact heat exchanger/heating element with a high power handling capability.

Figure 2:
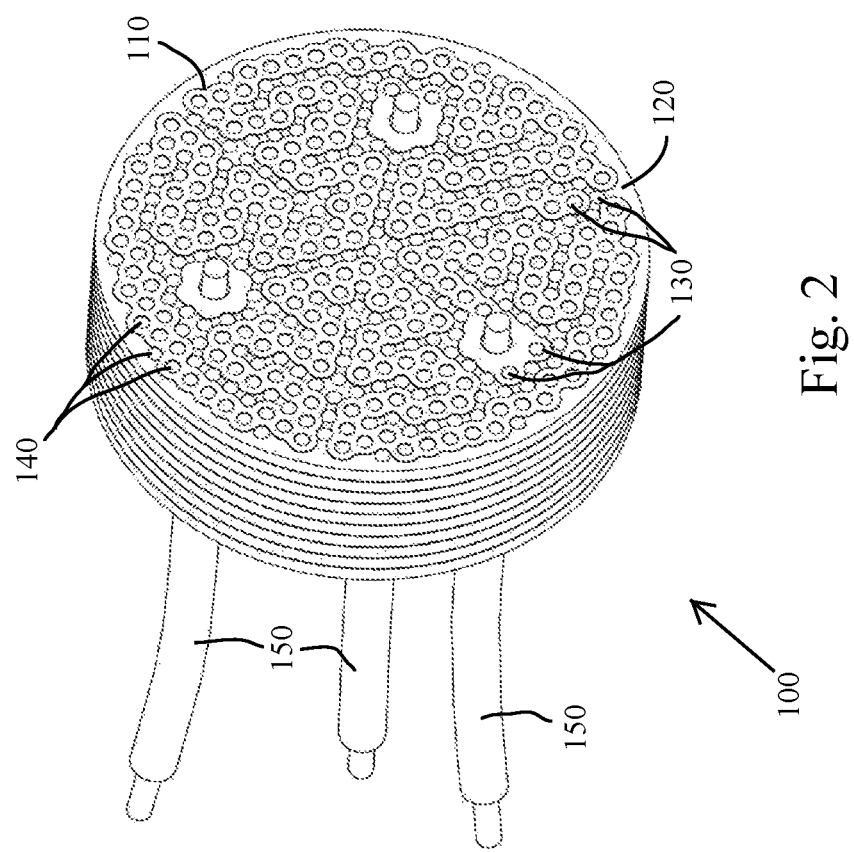
FIG. 2 is a perspective view of a heating element for use with a portable vaporizer.
Figure 3:
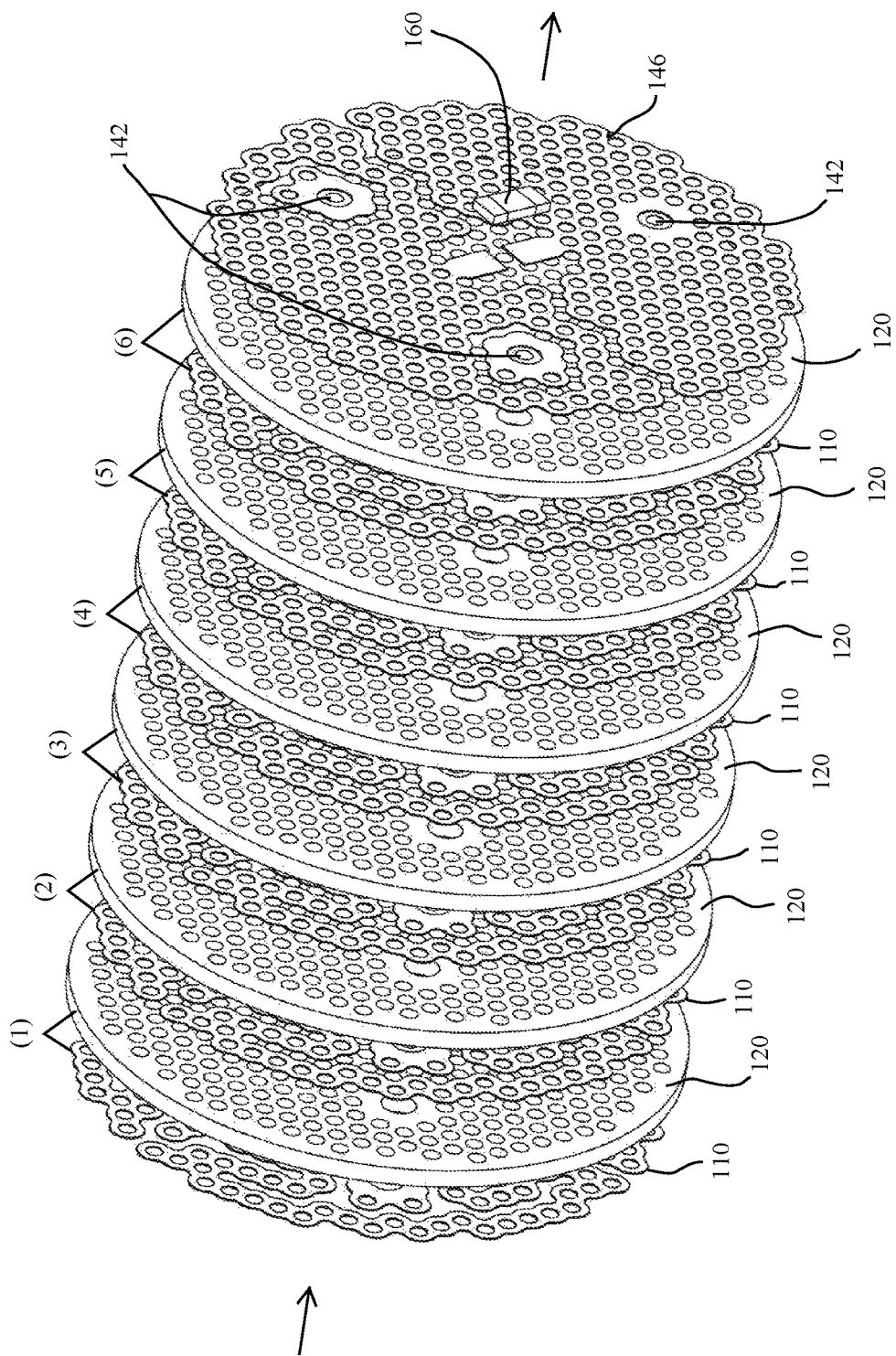
FIG. 3, is an exploded perspective view of a heating element for use with a portable vaporizer.
Figure 4:
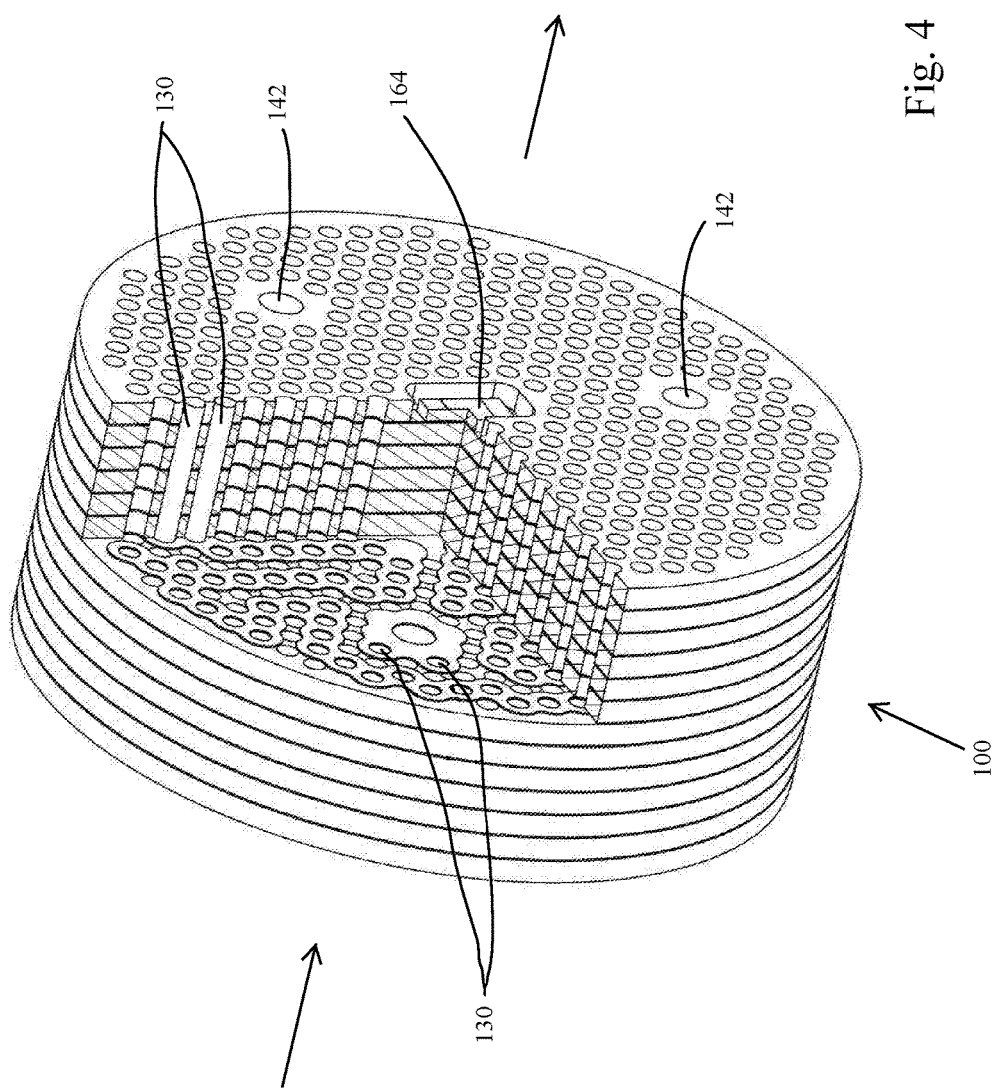
FIG. 4 is a perspective partial cut-away view of heating element for use with a portable vaporizer.

FIGS. 2-4 illustrate embodiments of the heating element 100. As shown, the heating element 100 is formed of a multilayered printed circuit board with alternating conductor 110 and dielectric/insulating 120 layers. The conductor layers 110 are connected with conductive vias 130 to form a resistive network, which may utilize both series and parallel combinations. That is, the conductor layers 110 act as resistors to an applied voltage/current, generating heat that is transferred to the electrically insulative but thermally conductive dielectric layers. The heating element 110 also includes an array of through-holes 140 through which the air passes and is heated. That is, air drawn into the vaporizer 10 through the air inlet apertures, passes through the nozzle 50 and then through the through-holes 140 of the heating element 100, where the air is heated to a desired temperature. In addition, the heating element includes wiring apertures 142 that provide access for power supply and sensor wires 150. FIG. 3 shows an exploded view of the heating element 100. In this exemplary embodiment, the heating element 100 includes six sets of alternating conductive layers 110 and insulating layers 120, which are labeled as layers (1)-(6).

As shown in the embodiments of FIGS. 2-4, the heating element 100 is a circular Printed Circuit Board manufactured using LTCC process equipment. The specific embodiment utilizes Co-fired Ceramic material for its high service-temperature ceiling, high thermal conductivity, and low outgassing properties. However, the same design can utilize common PCB materials such as FR4 or Polyimide resins through the use of standard PCB processing equipment. LTCC structures have a number of process-related advantages that result from their laminate construction. LTCC substrates are conventionally made up of multiple green tapes (i.e., uncured tapes) that are collated (stacked), laminated and fired (i.e., co-fired) to form a monolithic ceramic substrate, which in the present application forms the heating element. That is, LTCC devices are made by processing a number of layers independently and assembling them into a device as a final step prior to firing. This differs from semiconductor device fabrication where layers are processed serially; each new layer being fabricated on top of previous layers.

During manufacture of the heating element 100, thick film conductors are printed (e.g., screen printed) onto individual green tapes prior to collating and laminating the tapes. The green tapes typically contain a mixture of glass and ceramic fillers in a binder (e.g., organic binder). The conductors may be printed in any desired pattern on the surface of the green tape. Once the conductor pattern is formed on a layer of green tape, this layer of green tape and the printed thick film conductor may be punched to provide pilot apertures corresponding to the through-holes 140, wiring apertures 142 and vias 130 illustrated in FIG. 3. This process is repeated until a desired number of green tape/conductor layers are formed. The green tapes, along with their printed conductors, are then stacked and compressed together. The compressed tape layers may then be milled to define the through-holes, wiring apertures and vias. The vias are filled with a suitable conductive material prior to firing the stacked green tapes. Alternatively, the vias could be filled with conductive paste prior to stacking the green tapes. In any arrangement, the stacked tapes along with their conductors are then co-fired, during which organic binders within the stack are burned off and the remaining materials form, according to their compositions, ceramic and metallic materials. In the present application, the green tapes form the dielectric/insulating layers 120 and the printed thick film conductors form the conductive layers 110. Final shaping, milling and/or grinding may be performed after firing. Though discussed as including individual layers, it will be appreciated that, after firing, the heating element 100 is a monolithic structure.

The use of the LTCC process facilitates making the heating element extremely compact. For instance, in the illustrated non-limiting embodiment, the heating element has a diameter of about 9 mm and a thickness of about 3.6 mm. This embodiment of the heat exchanger includes approximately 400 through holes 140 each having a diameter of approximately 0.25 mm. In such an embodiment, the surface area of the generally cylindrical through holes extending through the thickness of the heat exchanger is approximately 1200 sq. mm for a heating element having an approximately 64 sq. mm end surface. That is, the heat exchanger area for air passing through the heating element is 10-20 times larger than the end surface area through which the air passes. Further, the combined area of openings of the through-holes in the end surface of the heating element is approximately 35% of the end surface area of the heating element. In this embodiment, approximately 35% of the material within the spatial envelope of the heating element is removed as a result of forming the through-holes. In such an embodiment, the heating element is capable of dissipating approximately 50 watts of power.

As noted, the conductor layers 110 may be formed in any desired pattern on the dielectric/insulating layers 120. However, it is desirable to enhance or maximize the conductor surface area to the ceramic surface area to improve the transfer of heat to the thermally conductive insulating layers 120, which form a majority of the surface area of the through-holes 140 and which primarily heat the air passing through the heating element. Along these lines, it is desirable, though not required, that the periphery of each through hole 140 be at least partially surrounded by the conductor 110. Such an arrangement facilitates provision of heat energy to the internal surfaces of the through-holes.

By changing the conductive layer count, via placement, conductor thickness and/or specific layout geometry, the resistance of the network can be customized over a wide range. This allows heating elements of various powers to be produced for a specific applied voltage. Additionally, multiple separate circuits can easily be incorporated into a single exchanger, allowing impedance-matching under a range of electrical conditions and battery states.

Figure 5B:
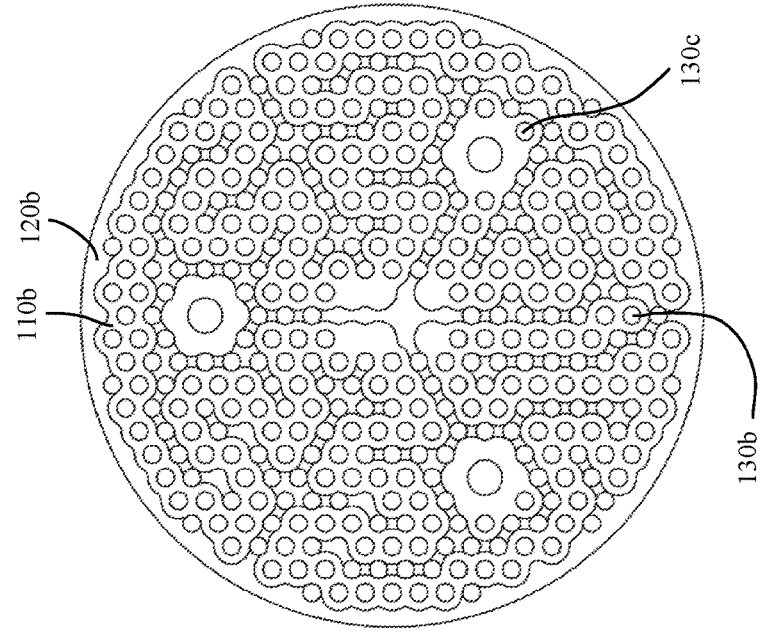
FIGS. 5A and 5B illustrate conductive layers disposed on dielectric layers for incorporation into a heating element.
Figure 5A:
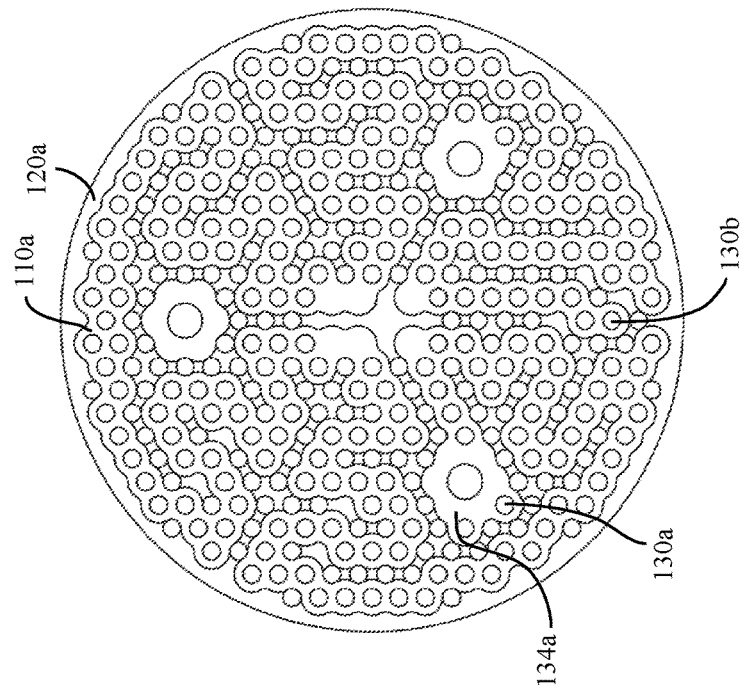

The ability to alter conductor layout and generate separate circuits within the heating element is illustrated in FIGS. 5A and 5B, which are presented by way of example and not by way of limitation. FIG. 5A illustrates one embodiment of a first conductor layer 110a as disposed on the surface of a first dielectric layer 120a. As shown, the conductor 110a is formed in a serpentine pattern between a first via 130a and a second via 130b. The illustrated serpentine pattern allows the conductor 110a to touch or surround each through-hole 140 in the dielectric layer 120a. That is, the illustrated pattern enhances the surface area of the conductor 110a to the dielectric layer 120a. In the illustrated embodiment, the first via(s) 130a are part of a conductor plate 134a, which may be attached to a power line. The second via 130b is a through-hole that was filled with conductive paste during firing of the heating element. See, e.g., FIG. 4. In any arrangement, the conductor 110a forms a resistive element between the first via 130a and the second via 130b in response to an applied current. The conductor of FIG. 5A may correspond to the first conductor/dielectric layer (1) illustrated in FIG. 3.

FIG. 5B illustrates a second conductor 110b as disposed on the surface of a second dielectric layer 120b. In this exemplary embodiment, the conductor/dielectric layer may correspond to layer (2), which is disposed adjacent to the conductor/dielectric layer (1) of FIG. 3. As shown, the second layer conductor 110b extends between the second via 130b and a third via 130c. In this arrangement, the conductor 110a of layer (1) is disposed in series with the conductor 110b of layer (2). This set of conductors may form its own electrical circuit and/or may be combined with additional conductors.

In one embodiment, the heating element utilizes sets of parallel circuits where each parallel circuit includes a series of two conductors. Referring to the six layer exemplary heating element of FIGS. 4 and 6, layers (1) and (2) may be connected in a first series circuit that is disposed in parallel with both a second series circuit (3) and (4) and a third series circuit (5) and (6). Use of the stacked sets of series circuits allows the heating element to dissipate significant amounts of power while being resistant to destructive overheating (e.g., thermal run away). As will be appreciated, if all six of the conductive layers were in series, the total resistance of the heating element would be significantly increased. Further, when air is drawn through the heating element, a temperature gradient develops across the heating element from the inlet to the outlet side as cool air enters and is heated from ambient to exit temperature. This causes conductive layers closer to the intake side to cool with respect to the outlet-side layers. Since electrical resistance is proportional to conductor temperature, the resistance of the intake side layers decreases with respect to the outlet side layers. Further, since power dissipation is proportional to resistance for a given current and current is equal through each of the six series layers, the power dissipation of the inlet-side layers decreases with respect to the outlet-side layers. This reinforces the temperature gradient and creates a positive feedback cycle that concentrates the power dissipation at the outlet side of the heating element. This decreases the power handling of the heating element and creates the potential for thermal runaway. Such a potential thermal runaway condition is at least partially enabled by a large temperature gradient (i.e., during airflow) across such a large single series circuit.

Figure 6:
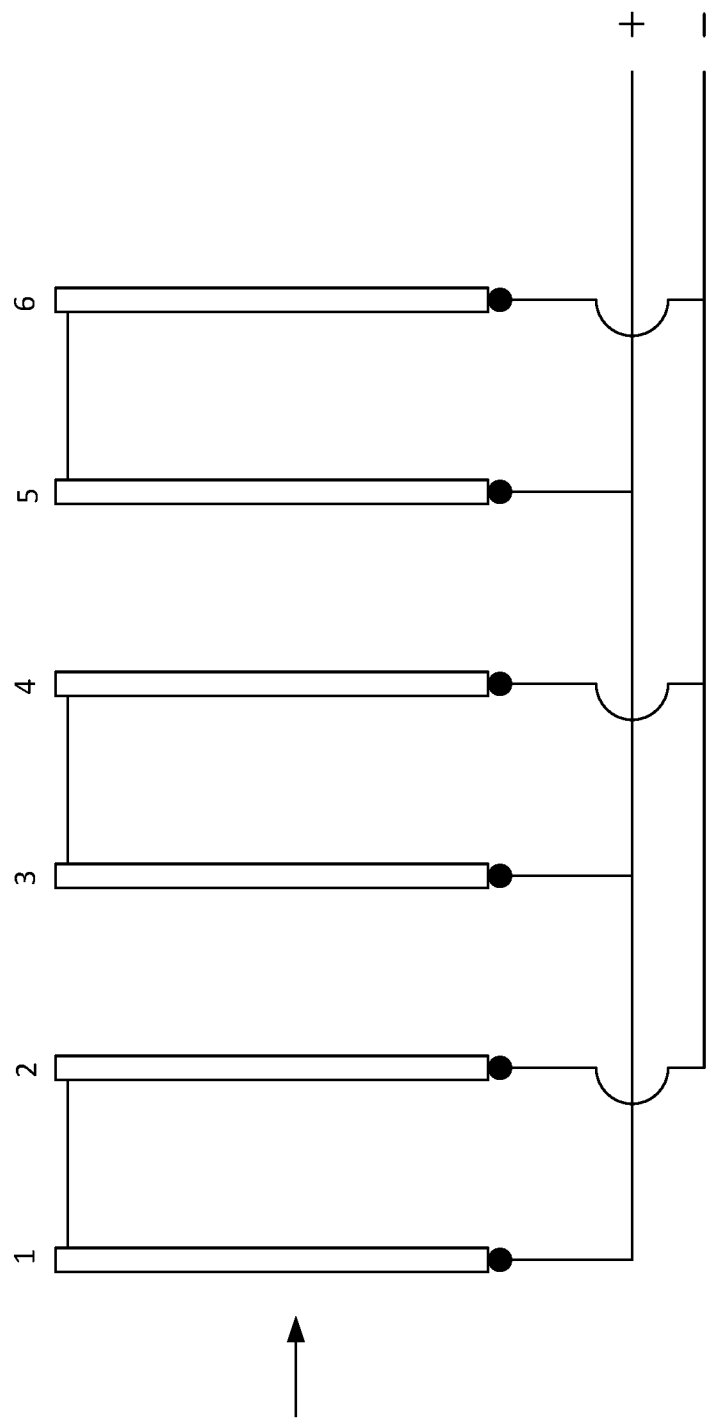
FIG. 6 illustrates one exemplary circuit arrangement for the heating element of FIG. 3.

Use of sets of series circuits disposed in parallel allows conductors/resistors toward the inlet to more readily dissipate power as they operate independently of the conductor/resistors toward the outlet. That is, as shown in FIG. 6, each series set of conductors (1)+(2), (3)+(4) and (5)+(6) sees the entire battery voltage. Further, due to the thin dielectric layer separating each pair of conductors/resistors (i.e., close proximity of the conductors), each pair of conductors/resistors in each circuit are effectively at the same temperature. When air flows through the heating element, the air inlet side pair of conductors (1)+(2) are cooled, lowering their resistance and allowing the dissipation of additional power. Alternately, the air outlet side series set (5)+(6) increases in temperature, raising its resistance and lowering its power dissipation. Each individual series set is still experiencing a gradient driving it toward thermal runaway (i.e., the resistor closer to the inlet side is hotter and dissipates fractionally more power than its series counterpart). However, the series circuit only spans the temperature gradient between two adjacent layers as opposed to the entire heating element.

The heating elements 100 of FIGS. 2-4 may include a number of additional components. For instance, the heating element of FIG. 3 includes a heat spreader 146 mounted on the face of the last conductor/dielectric layer (6) opposite of the conductor 110. This heat spreading layer 142 is made of the same material as the conductor layers and helps spread heat to a surface mounted thermistor 160. The resistance of the thermistor 160 changes proportionally to the exit airflow temperature, allowing control of the power applied to the heating element based on the exit airflow temperature. The is, the thermistor 160 may connect to the control circuit 70 by a sensor wire and the control circuit may control the operation of the heating element based at least in part on an output of the thermistor.

The heating element of FIG. 4 incorporates two embedded temperature sensors 164 (e.g., thermistors, thermocouples etc.; only one illustrated) in inlet and outlet sides of the heating element 100. The thermistors could also be surface-mounted or through-hole mounted depending on specific design and process constraints. In this embodiment, airflow through the heating element causes a temperature differential to develop between the inlet and outlet side. Monitoring this differential and the applied power provides information that can be used to derive the airspeed through the heat exchanger and means of measuring both inlet and outlet temperatures.

While primarily described with respect to an exemplary vaporizer, the design and disclosure related to the heating element is not intended to be so limited. The heating element may be used in other applications where compact, high output airflow heating is desired.

The foregoing description has been presented for purposes of illustration and description. Furthermore, the description is not intended to limit the inventions and/or aspects of the inventions to the forms disclosed herein. Consequently, variations and modifications commensurate with the above teachings, and skill and knowledge of the relevant art, are within the scope of the presented inventions. The embodiments described hereinabove are further intended to explain best modes known of practicing the inventions and to enable others skilled in the art to utilize the inventions in such, or other embodiments and with various modifications required by the particular application(s) or use(s) of the presented inventions. It is intended that the appended claims be construed to include alternative embodiments to the extent permitted by the prior art.

What is claimed is:

1. An herbal vaporizer, comprising:
   an elongated housing including a power source;
   an herb vaporization chamber attached to an end of the elongated housing, wherein an inlet of the herb vaporization chamber is in fluid communication with an air inlet port of the vaporizer and an outlet of the herb vaporization chamber is in fluid communication with an outlet port of the vaporizer; and
   a convective heating element disposed within an airflow path between the air inlet port and the outlet of the herb vaporization chamber and being selectively connectable to the power source, the convective heating element having:
      an air inlet end;
      an air outlet end;
      a plurality of spaced conductor layers disposed between the air inlet end and the air outlet end, wherein each the conductor layer is substantially parallel to the air outlet end and the conductive layers are electrically connected in at least a first resistive network;
      a plurality of through-holes extending through the convective heating element between the air inlet end and the air outlet end.

2. The device of claim 1, wherein the convective heating element further comprises:
   a plurality of insulating layers, wherein at least one insulating layer is disposed between each adjacent pair of the conductor layers.

3. The device of claim 2, wherein the insulating layers comprise co-fired ceramic tape layers and the conductor layers comprise thick film conductors printed on the tape layers.

4. The device of claim 3, wherein the convective heating element is a monolithic structure.

5. The device of claim 2, further comprising:
   at least one conductive via extending through at least one insulating layer to electrically connect at least two of the conductor layers.

6. The device of claim 2, further comprising:
   at least first and second wiring apertures extending through at least a portion of the convective heating element between the inlet end and the outlet end; and
   at least first and second power supply wires extending through the wiring apertures, wherein the first and second power supply wires are each electrically connected to at least a portion of the conductor layers to define at least a first electrical circuit with the power source.

7. The device of claim 1, wherein a first set of the conductor layers define a first electrical circuit and a second set of the conductor layers define a second electrical circuit.

8. The device of claim 7, wherein the first electrical circuit comprises a first series circuit of at least two of the conductor layers and the second electrical circuit comprises a second series circuit of at least two different conductor layers.

9. The device of claim 8, wherein the first electrical circuit and the second electrical circuit are disposed in parallel.

10. The device of claim 1, wherein, the plurality of through-holes are substantially perpendicular to the conductor layers.

11. The device of claim 10, wherein each of the conductor layers borders at least a portion each the plurality of though-holes.

12. The device of claim 1, wherein the convective heating element comprises a substantially cylindrical element wherein the air inlet end and the air outlet end form ends of the cylindrical element.

13. The device of claim 12, wherein a total combined surface area of inside surfaces of the through-holes between the air inlet end and the air outlet end is at least ten (10) times the surface area of the air inlet end.

14. The device of claim 12, wherein a combined volume of the through holes is at least one-fourth of the volume of the convective heating element as defined between the air inlet end and the air outlet end.

15. The device of claim 12, wherein a diameter of the substantially cylindrical element is less than 15 mm.

16. The device of claim 15, wherein a diameter of the substantially cylindrical element is less than 10 mm.

17. The device of claim 1, further comprising:
   at least a first temperature sensor attached to the convective heating element; and
   a controller configured to control application of power from the power source to the convective heating element based at least in part on an output of the temperature sensor.

18. The device of claim 17, further comprising:
   a temperature adjustment controller for adjusting a vaporization temperature of air heated by the convective heating element.

19. The device of claim 1 wherein the convective heating element includes at least six conductor layers.

* * * * *